United States Patent
Staton et al.

(10) Patent No.: US 10,376,423 B2
(45) Date of Patent: Aug. 13, 2019

(54) WEARABLE PRODUCTS HAVING SENSING AND RESPONSE COMPONENTS

(71) Applicant: NEWTONOID TECHNOLOGIES, L.L.C., Liberty, MO (US)

(72) Inventors: Fielding B. Staton, Liberty, MO (US); David Strumpf, Columbia, MO (US)

(73) Assignee: NEWTONOID TECHNOLOGIES, L.L.C., Liberty, MO (US)

( * ) Notice: Subject to any disclaimer, the term of this patent is extended or adjusted under 35 U.S.C. 154(b) by 0 days.

(21) Appl. No.: 15/923,769

(22) Filed: Mar. 16, 2018

(65) Prior Publication Data

US 2018/0263826 A1 Sep. 20, 2018

Related U.S. Application Data

(60) Provisional application No. 62/473,096, filed on Mar. 17, 2017.

(51) Int. Cl.
| | |
|---|---|
| *A61F 13/15* | (2006.01) |
| *A61F 13/42* | (2006.01) |
| *A61B 5/00* | (2006.01) |
| *A61H 1/00* | (2006.01) |
| *A61B 5/20* | (2006.01) |
| *A61F 13/49* | (2006.01) |
| *A61F 13/84* | (2006.01) |
| *A61F 13/00* | (2006.01) |
| *A61B 5/145* | (2006.01) |
| *A61B 90/00* | (2016.01) |

(52) U.S. Cl.
CPC .......... *A61F 13/42* (2013.01); *A61B 5/0022* (2013.01); *A61B 5/14507* (2013.01); *A61B 5/207* (2013.01); *A61B 5/6804* (2013.01); *A61B 5/6808* (2013.01); *A61B 5/6833* (2013.01); *A61B 5/742* (2013.01); *A61B 5/7405* (2013.01); *A61B 5/7455* (2013.01); *A61B 5/7465* (2013.01); *A61F 13/00063* (2013.01); *A61F 13/49* (2013.01); *A61F 13/84* (2013.01);

(Continued)

(58) Field of Classification Search
CPC .............. A61F 13/04; A61F 13/49; A61F 2013/00089; A61F 2013/15146; A61F 2013/426
USPC .................................................. 604/361, 362
See application file for complete search history.

(56) References Cited

U.S. PATENT DOCUMENTS

| | | | |
|---|---|---|---|
| 9,005,101 B1 | 4/2015 | Van Erlach | |
| 2004/0220538 A1* | 11/2004 | Panopoulos | A61F 13/42 604/361 |

(Continued)

OTHER PUBLICATIONS

PCT Application No. PCT/US2018/022954, International Search Report and Written Opinion, dated May 31, 2018, 11 pages.

(Continued)

*Primary Examiner* — Jacqueline F Stephens
(74) *Attorney, Agent, or Firm* — Lathrop Gage L.L.P.

(57) ABSTRACT

A system for monitoring at least one characteristic of biological material of an individual includes a wearable product. The wearable product includes an outer surface and a skin contact surface defining an internal area. An analysis portal is disposed in the internal area, and includes a sensing portion and an investigation portion. The sensing portion has at least one sensor, and the investigation portion that includes a computing device having a health screener. The sensing portion of the analysis portal comes into contact with a biological material of the individual, and the health screener is configured to determine at least one characteristic of the biological material. The computing device is communicatively coupled to the sensors and the display.

20 Claims, 11 Drawing Sheets

(52) U.S. Cl.
CPC ............... *A61H 1/00* (2013.01); *A61B 5/447* (2013.01); *A61B 2090/065* (2016.02); *A61B 2503/04* (2013.01); *A61F 2013/00089* (2013.01); *A61F 2013/15146* (2013.01); *A61F 2013/424* (2013.01); *A61F 2013/426* (2013.01); *A61F 2013/8473* (2013.01)

(56) References Cited

U.S. PATENT DOCUMENTS

| | | |
|---|---|---|
| 2005/0099294 A1 | 5/2005 | Bogner et al. |
| 2010/0160882 A1* | 6/2010 | Lowe .................. A61F 13/42 604/361 |
| 2010/0249560 A1 | 9/2010 | Levinson et al. |
| 2011/0054285 A1 | 3/2011 | Searle et al. |
| 2015/0087935 A1 | 3/2015 | Davis et al. |
| 2016/0275775 A1 | 9/2016 | Glasgow et al. |

OTHER PUBLICATIONS

New Atlas, FDA Approved Viberect Device for Treatment of Erectile Dysfunction, www.newatlast.com/viberect-device/19312/, dated May 17, 2018, 3 pages.

Therapeutic Advances in Urology, Shockwave Treatment of Erectile Dysfunction, www/ncbi.nlm.nih.gov/pmc/articles/PMC36074921, dated Apr. 2013, 7 pages.

* cited by examiner

| Name 304 | Results 308 | Date/Time 310 | Alert 318 | Recommendation 320 |
|---|---|---|---|---|
| John | Protein: Normal<br>Color: Clear<br>*<br>*<br>*<br>Sugars: 300 mg/dL<br>Bacteria: Normal | 11/1/2016<br>14:00 | High Blood Sugar | Check blood glucose and administer 1 unit insulin |

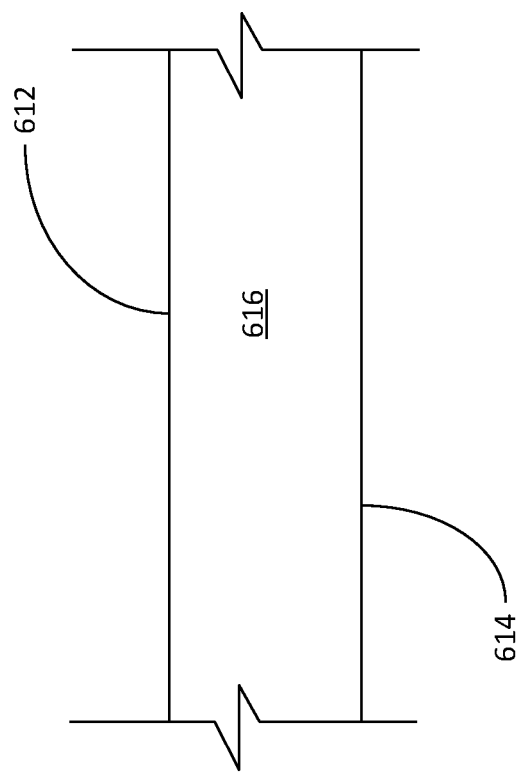

WEARABLE PRODUCTS HAVING SENSING AND RESPONSE COMPONENTS

CROSS-REFERENCE TO RELATED APPLICATIONS

This application claims priority to U.S. Provisional Patent Application No. 62/473,096, filed Mar. 17, 2017, the entirety of which is incorporated herein by reference.

FIELD OF THE INVENTION

The invention relates to wearable products having sensing and response components and systems, such as diapers, bandages, and articles of clothing.

BRIEF DESCRIPTION OF THE FIGURES

FIG. 4 shows an example user record created by the investigation portion of the analysis portal.

FIG. 11 illustrates a cross-sectional view of the pad of FIG. 10.

SUMMARY

Figure 1:
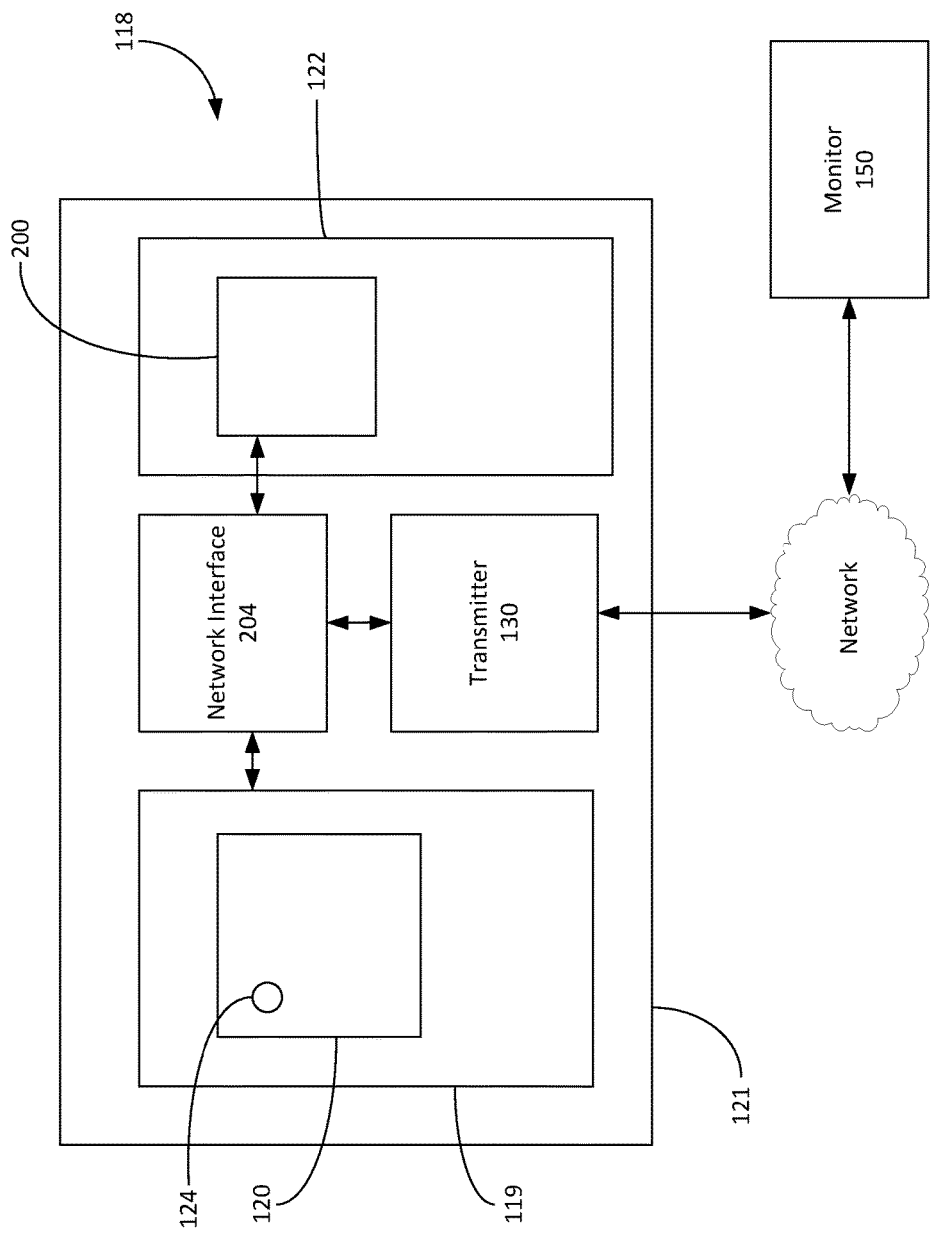
FIG. 1 is a block diagram of an analysis portal according to one embodiment of the invention.

The following presents a simplified summary of the invention in order to provide a basic understanding of some aspects of the invention. The summary is not an extensive overview of the invention. It is not intended to identify critical elements of the invention or to delineate the scope of the invention. Its sole purpose is to present some concepts of the invention in a simplified form as a prelude to the more detailed description that is presented elsewhere.

In one embodiment, a system for monitoring at least one characteristic of biological material of an individual includes a wearable product. The wearable product includes an outer surface and a skin contact surface defining an internal area. An analysis portal is disposed in the internal area, and includes a sensing portion and an investigation portion. The sensing portion has at least one sensor, and the investigation portion that includes a computing device having a health screener. The sensing portion of the analysis portal comes into contact with a biological material of the individual, and the health screener is configured to determine at least one characteristic of the biological material. The computing device is communicatively coupled to the sensors and the display.

In another embodiment, a system for monitoring at least one characteristic of a biological material of an individual has a wearable product with an analysis portal and a pad. The analysis portal includes a sensing portion comprising at least one sensor, and an investigation portion comprising a computing device having a health screener. The pad has a vibrating motor, and the vibrating motor is selectively activated to provide vibrations to the individual when the wearable product is within a predetermined distance from the pad. The sensing portion of the analysis portal comes into contact with a biological material of the individual. The health screener is configured to determine at least one characteristic of the biological material. The computing device initiates an alert based on the at least one characteristic of the biological material.

In still another embodiment, a system for influencing a biological attribute of an individual comprises a pad that has a contact surface and a bottom surface defining an interior area therebetween. An electric panel is disposed adjacent the interior area, and includes a sensor; and a vibrating motor which is selectively activated causing the pad to vibrate.

DETAILED DESCRIPTION

Much information about a person may be gleaned from their bodily excretions. Indeed, many doctors rely on urinalysis to deduce various maladies plaguing an individual. Urine is a complex biofluid. Studies indicate that human urine may include over 3,000 detectable compounds and other substances. A healthy adult having a normal fluid intake of about 2 liters a day typically has a daily urine output of between 800 to 2,000 milliliters. Approximately 95% of a healthy individual's urine is water. The remainder mainly consists of solutes (i.e., chemicals which may be dissolved in water). Some of the solutes may be the result of normal or abnormal biochemical activity within the cells of the human body, whereas other solutes may be due to chemicals that originated outside the body (e.g., pharmaceuticals or other drugs). In general, the solutes within the urine of a healthy individual may be classified into two groups—organic molecules and ions. The organic molecules may be electrically neutral and may be larger in size relative to the ions. These organic molecules may include, for example, urea, creatinine, uric acid, enzymes, hormones, carbohydrates, etc. The ions in the urine are either positively or negatively charged, and may include, for example, Sodium ($Na^+$), Potassium ($K^+$), Magnesium ($Me^{2+}$), Calcium ($Ca^{2+}$), Ammonium ($NH^{4+}$), Sulfates ($SO_x$), Phosphates ($H_2PO_4^-$, $HPO_4^{2-}$, $PO_4^{3-}$), etc.

The skilled artisan understands that analysis of the urine of an individual, including of the constituents thereof, can offer key insights about the individual's short-term and long-term health and overall well-being. For example, the skilled artisan appreciates that sugars are discharged in a healthy individual's urine at no more than 110 mg/dl. In diabetics, however, this number may increase to several hundred mg/dl, and even several thousand mg/dl. Thus, exorbitant amounts of sugar or ketones in one's urine may indicate that the individual is diabetic and/or that his kidneys are damaged or diseased. Similarly, the presence of the Leukocyte Esterase enzyme in one's urine may indicate that the individual is currently suffering from a urinary tract infection. An abnormally high specific gravity of an individual's urine may indicate that the individual is currently dehydrated. Presence of Bilirubin in one's urine may suggest liver disease. Presence of large amounts of proteins in a person's urine may indicate that the person has proteinuria.

Presence of blood or myoglobin in the individual's urine may indicate that the individual suffers from hematuria. An upward trending alcohol content of the urine may indicate that the user is continually consuming alcoholic beverage(s). And so on. Indeed, the skilled artisan appreciates that the appearance (e.g., color) of the urine, its pH, its volume, its contents, its concentration, its temperature, its smell, the pressure at which it is voided and its flow rate, etc., may all provide valuable insights into an individual's health and well-being.

A person's sweat may also be a window into a person's immune system. For example, sweat tests are used to determine the level of chloride in sweat, which may be used to diagnose cystic fibrosis. In the U.S., newborn screenings routinely include sweat tests to assess for cystic fibrosis. Furthermore, it is obvious that a person's blood may be analyzed for the purpose of detecting many different types of ailments.

Typically, urinalysis, sweat test analysis, blood work, etc. is conducted in a lab. For example, an employer screening a potential employee for recreational drugs may send the employee to a lab for urinalysis. A sports team may require its players to go to a lab for urinalysis and the screening of performance enhancing drugs. A patient having back pain may likewise be ordered by a doctor to go to a lab for urinalysis and/or blood work. Such may inconvenience the test taker (e.g., a person may have to take several hours out of his day to drive to a lab for the testing of a sample of his biologic material), or may be rendered nearly impossible due to limitations of the patient (e.g., babies, persons having limited mobility, etc.). Because of this inconvenience, and the costs associated with lab analyses, even health conscious individuals generally have tests only when required to do so. Since these tests may provide key insights into an individual's health and well-being, it may be desirable to provide individuals the opportunity to have these tests conducted more regularly and conveniently. It may also be desirable to securely store results of these tests and to provide the test taker (or the test taker's trusted advisor) individualized and real-time and/or near-time feedback based on the results of the urinalysis. It may therefore be desirable to have a wearable product that is configured to analyze readily available information from a person's body and provide that data to an interested party or system for taking controlled action.

Wearable products having sensing and response components and systems are described herein. Referring first to FIG. 1, a wearable product 100 may be equipped with an analysis portal 118 which includes a sensing portion 119 and an investigation portion 122. The sensing portion 119 may include one or more sensors 120. The sensing portion 119 and the investigation portion 122 may be provided within a housing 121 to prevent untimely or premature failure due to contact with bodily fluids.

The sensor 120 may include one or more fluid accepting portions 124. The fluid accepting portion 124 may be configured to accept fluids (e.g., urine of a user, sweat, blood, etc.) In combination with the housing, the fluid accepting portion 124 may be configured to come into direct contact with fluids. The sensor 120 may be configured to come into direct contact with the fluid without adverse effects. The sensors 120 may include, but shall not be limited to: temperature sensors, optical (e.g., blood oxygen, spectroscopy), blood alcohol sensors, bacteria sensor, olfactory sensors (e.g., conducting polymer sensor), other biosensors (e.g., devices that convert or transduce a biological response into an electrical signal), and/or any other sensors which may be used for "lab-on-a-chip" applications, whether now known or subsequently developed. Each sensor 120 may be respectively configured to sense and/or determine (e.g., qualitatively or quantitatively) a characteristic of the fluid that the sensor is contacting.

In one embodiment, the analysis portal 118 may be configured for multiple uses. The analysis portal 118 may be programmed in conjunction with an output device (e.g., monitor 150) to receive analysis results. The monitor 150 may include a smart phone, for example. A mobile application may be downloaded onto the mobile phone to engage with the analysis portal 118. The analysis portal 118 may include a rechargeable battery and/or capacitive storage element which may receive power from solar charging, electricity (e.g., wired charge), or other methods now known or later developed.

In another embodiment, the analysis portal 118 is configured for disposable use. Here, to maintain reasonable costs, the analysis portal 118 may be equipped with relatively unsophisticated sensors 120 (e.g., as compared to the sensors 120 which may be utilized with a non-disposable analysis portal 118). For example, in one embodiment, the sensor 120 may be a simple moisture sensor 120 used to detect the presence of moisture at or near the wearable product 100.

As is described in greater detail below, the analysis portal 118 may be disposed (e.g., secured or otherwise situated) in or on a wearable product 100 in an appropriate place such that the sensing portion 119 may come into contact with the desired fluid. In some embodiments, the sensing portion 119 may include pits, channels, or other indentations in order to temporarily retain fluids. The sensors 120 may be located in the pits or channels. It shall be understood by those of skill in the art that the analysis portal 118 may take a variety of configurations, so long as the measurable fluid is able to come into contact with the sensing portion 119 in order to allow the sensor(s) 120 to measure different characteristics of the fluid sample. It shall be further understood that multiple sensors 120 may be disposed on or in the sensing portion 119 for measuring many different types of characteristics.

In order to ensure that the analyses of the bodily fluid samples are as accurate as possible, the sensors 120 may require periodic cleaning. For instance, remnant blood or urine may adversely affect the readings of a sensor for detecting the presence of certain bacteria in a sample. Thus, as will be further understood from the examples below, in embodiments where the analysis portal 118 is configured for recurring use, the sensors 120 (and potentially even the entire analysis portal 118) may be removable from a wearable product 100 for cleaning as is discussed in more detail below. Additionally, some embodiments may include a cleansing agent or solvent delivery pouch that is biocompatible with the user and allows metered delivery of the cleansing agent to the surface that is intended to be analyzed.

Figure 2:
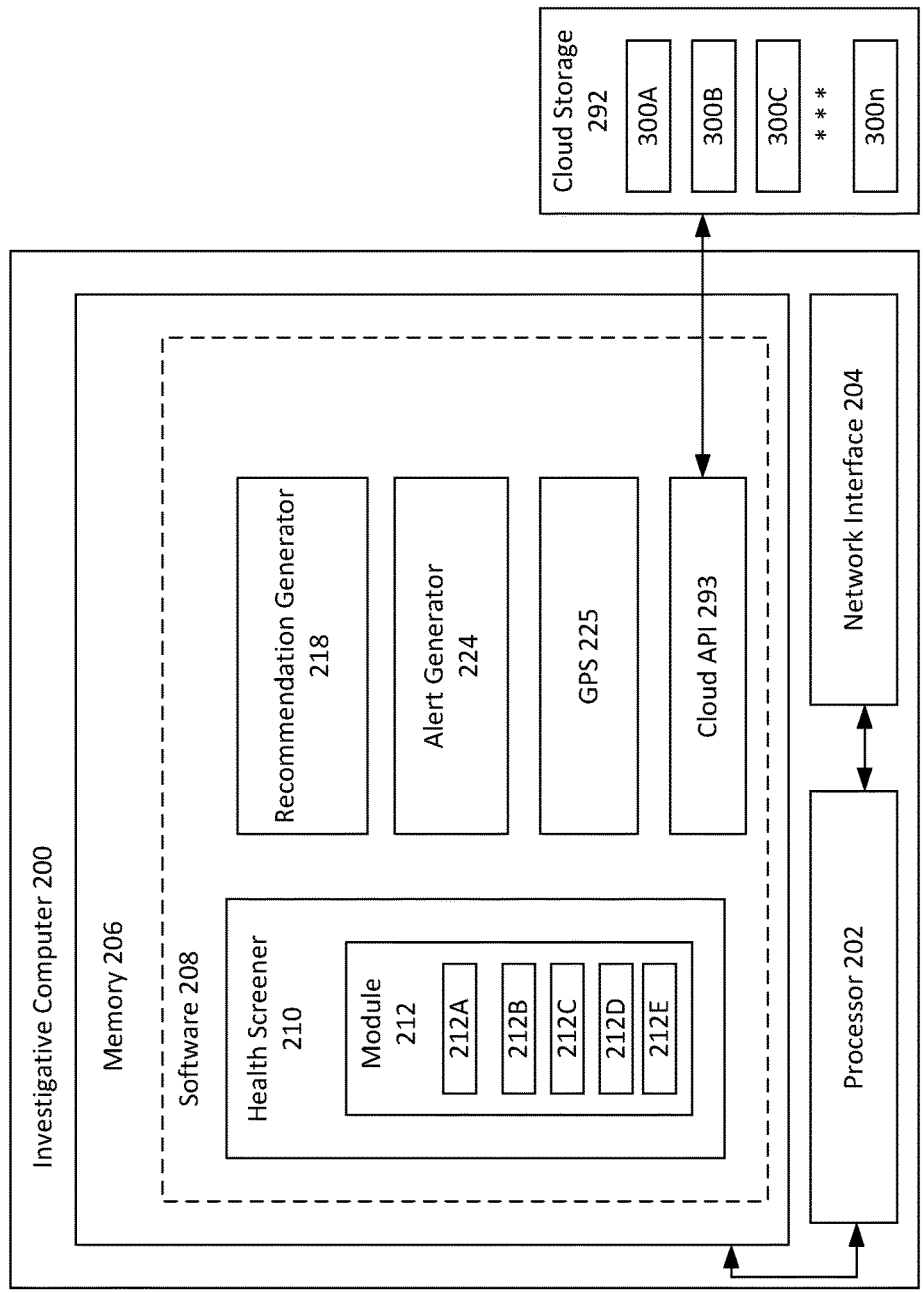
FIG. 2 is a block diagram of an investigative computer of the analysis portal according to an embodiment of the invention.

The investigation portion 122 may be communicatively (e.g., electronically via wires or wirelessly) coupled to the sensing portion 119 for completing the evaluations of the fluid samples taken by the one or more sensors 120. An output may be generated in response. The investigation portion 122 may include an investigative computer 200 (FIG. 2). The investigative computer 200 includes a processor 202 communicatively coupled to a network interface 204 and memory 206. Processor 202 represents one or more digital processors. In some exemplary embodiments, the processor 202 may be configured through particularly configured hardware, such as an application specific integrated circuit (ASIC), field-programmable gate array (FPGA), etc., and/or through execution of software algorithms to perform functions in accordance with the disclosure herein. Network interface 204 may be implemented as one or both of a wired network interface and a wireless network (e.g., Wi-Fi, Internet, Bluetooth, low-frequency RF, infrared, visible light modulation, etc.) interface, as is known in the art. Memory 206 represents one or more of volatile memory (e.g., RAM) and non-volatile memory (e.g., ROM, EEPROM, FRAM, FLASH, magnetic media, paramagnetic materials, optical media, etc.). Although shown within the investigative computer 200, memory 206 may be, at least in part, implemented as network storage that is external to the analysis portal 118 and accessed via network interface 204.

Software 208 may be stored in a transitory or non-transitory portion of the memory 206. Software 208 includes machine readable instructions that are executed by processor 202 to perform the functionality of the investigation portion 122 as described herein. In the illustrated example, the software 208 optionally contains a health screener 210, a recommendation generator 218, an alert generator 224, and a global positioning system 225, each of which are described in more detail below.

The health screener 210 may be configured to evaluate the readings obtained from the sensors 120. Specifically, the health screener 210 may have a module 212 (e.g., code to implement one or more routines) associated with each of the sensors 120. For instance, if the sensors 120 are respectively configured to sense and/or detect drugs, proteins, color, pressure, sugars, stress levels, temperature, cancer cells, virus cells, and bacteria of or within a fluid or biological sample, the health screener 210 may include, but is not limited to, a drug module, 212A, a protein module 212B, a color module 212C, a pressure module 212D, a sugars module 212F, a temperature module 212G, and an infectious agent module 212H. Each module 212 may be configured to evaluate the particular reading obtained by the associated sensor 120 to determine whether the characteristic being evaluated is normal or is cause for concern.

For example, one or more of the modules 212 may, in embodiments, include or have access to memory (e.g., memory 206) containing average (i.e., normal) values for the particular characteristic being evaluated. For instance, and as discussed above, sugars are discharged in a healthy individual's urine at no more than 110 mg/dl. The sugars module 212F associated with the sugar sensor 120 in a wearable product 100 which comes into contact with urine (as descried below) may therefore have this threshold value of 110 mg/dl stored thereon or otherwise accessible thereto, so that when the urine of a user is tested, the sugars module 212F of the investigation portion 122 can evaluate whether the sugar level thereof is normal or is a cause for concern. If the sugar sensor 120 determines that the quantity of sugars in the urine sample is 50 mg/dl, the sugars module 212F may determine that the urine of the user does not contain excessive sugars. The sugars module 212F may also be configured to determine that the urine indicates that the user has low sugar. Alternately, if the sugar sensor 120 determines that the quantity of sugars in the urine sample is 300 mg/dl, the sugars module 212F may determine that the user's urine contains excessive sugar. Those of skill in the art understand that blood sugar may alternatively be measured in a person's blood sample according to known methods.

As another example, where a drug module 212A is intended to determine the presence of, for example, a pharmaceutical or recreational drug in the sample fluid, the drug module 212A may have access to information outlining the various parameters for detecting the presence of a drug Similar functionality shall be recognized by the other respective sensors as is understood by those of skill in the art.

The investigation portion 122, via a transmitter 130, may initiate a controlled response based on the evaluation of the one or more readings obtained from the sensors 120. For example, the analysis portal 118 may be in contact with a monitor 150, which may be used to communicate results from the analysis portal 118 to the user of the wearable product 100 or to someone who has been given access to receive information from the access portal 118.

The alert generator 224 of the software 208 may generate an alert based on information received by the sensors 120. For example, if a moisture sensor 120 detects the presence of moisture at or near the wearable product 100, the alert generator 224 may generate an alert. The alert may be auditory, visual, or other type of alert, and may be communicated in any number of ways. For example, in an embodiment, the alert generator 224 may transmit an alert message to the monitor 150. In some embodiments, the alert message may also be communicated to third parties. For instance, the alert message may be communicated to a user's physician, or other authorized third party. The alert may also coincide with a controlled response stimulus delivery of drug(s) or cleaning agents (saline, antibiotics, pain relievers, etc.) to the analyzed surface of the user.

Figure 3:
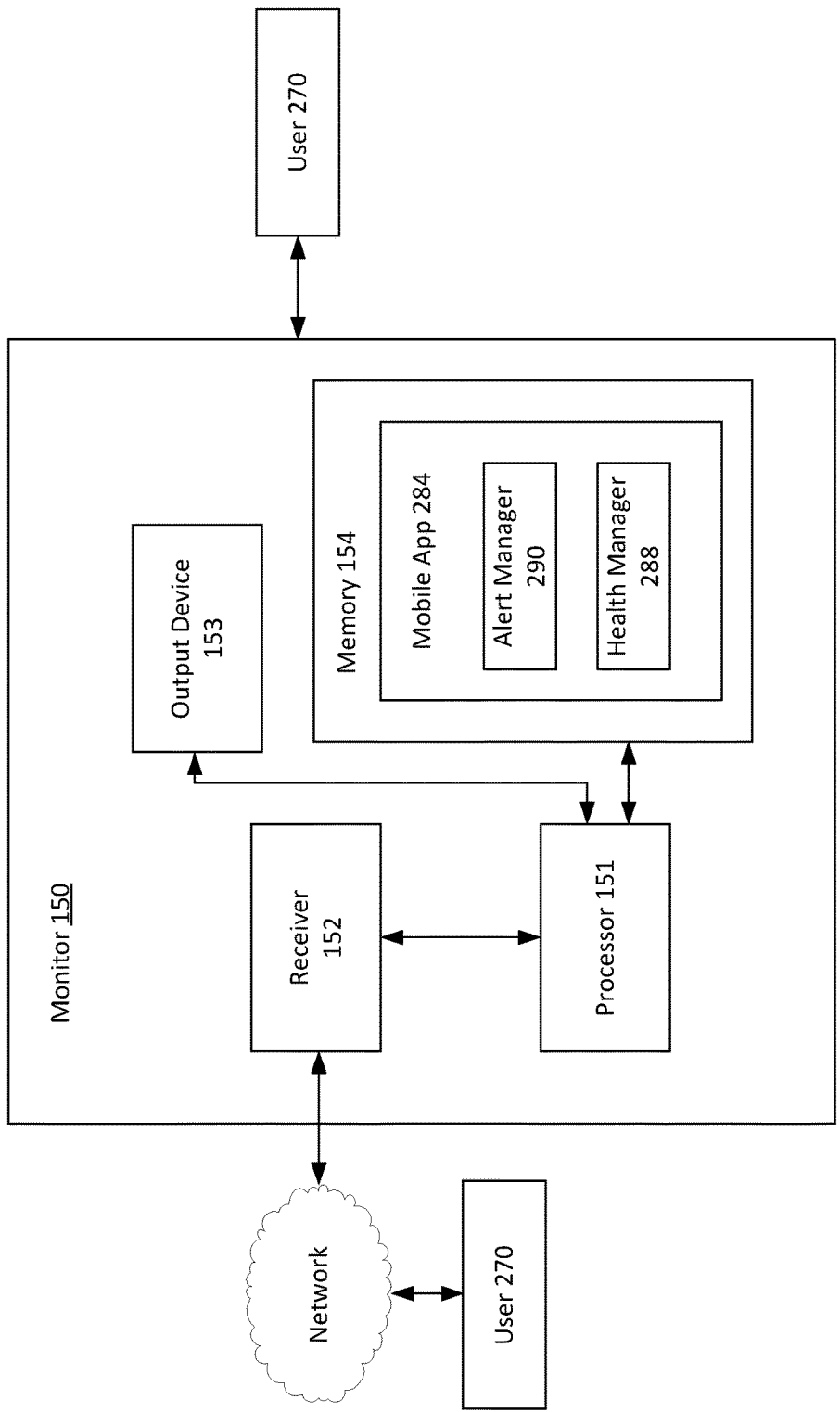
FIG. 3 is a block diagram of a monitor which interacts with the analysis portal according to an embodiment of the invention.

The monitor 150 may be, for example, a smart phone, computer, a PDA, a telemedicine remote device, a localized nearby subsystem accessory device, a specific-use mobile handheld unit, an embedded chip-on-board device, or a combination thereof. In some embodiments it may be desirable for the monitor 150 to be portable, though portability may not be desired in other (e.g., institutional) environments. As shown in FIG. 3, the monitor 150 may include a processor 151 in data communication with the receiver 152, an output device 153 (e.g., a screen), and non-transitory computer memory 154. As will be appreciated by those skilled in the art, the processor 151 may include multiple processors that work together. The receiver 152 may be particularly configured to receive a signal from the transmitter 130 of the analysis portal 118. The memory 154 may include a mobile application 284 for interacting with the analysis portal 118 and/or cloud-based memory as described in greater detail below.

The alert generator 224 may further transmit (e.g., via transmitter 130) a recommendation for taking action to the monitor 150. Based on the recommendation, the person receiving the alert may take appropriate action. An alert manager 290 may allow the user to customize the way in which alerts are communicated to the person(s) receiving the alert. For instance, where the user is a diabetic, the user may configure the alert manager 290 such that the monitor 150 beeps (and/or vibrates) each time a urinalysis indicates the user's sugar levels are above (or below) some user-defined threshold. Alternately, where the user knows that he has urinary tract infection, for example, he may configure the alert manager 290 such that alerts generated by the alert generator 224 regarding a urinary tract infection are automatically discarded for a given user-defined or other time period. Or, the user may indicate a time period threshold for the pressure/movement sensors such that, upon meeting the threshold, an alert is generated.

In embodiments, the fluid analysis results of the user may be encrypted and stored on secure network storage. For example, the results of the user may be encrypted and stored on the "cloud" 292. The investigative computer 200 may have a cloud API 293 which may allow the wearable product 100 (e.g., via the analysis portal 118) to securely communicate with the cloud 292. As can be seen, the cloud (or other secure network storage) 292 may include a plurality of records 300A-300N associated with the user. And the cloud storage may likewise include records of other users. Raw data delivery may be delivered to remote collection devices (including the "cloud") in the form of discrete quantitative sample values, delta-compression data packets (e.g. ADPCM), and other compression formats including lossless compression techniques intended to retain all raw data information. A variety of data profiling techniques (i.e. token encoding) may be used in order to characterize and minimize patterns of data while avoiding redundant and overly large datasets for communication transport.

The health manager 288 may, in embodiments, store and allow the user (or authorized third party) to access the results of fluid analysis conducted by an analysis portal 118 connected with a wearable product 100. For example, the health manager 288 may store the results from the various health screeners 210 incorporated into an analysis portal 118. These results may be time and date stamped, and may afford the user (or authorized third party) an opportunity to monitor health on a regular basis. The health manager 288 may be configured to aggregate data from several different analysis portals 118 (e.g., incorporated into wearable products 100 worn by multiple people) for reporting aggregate results, e.g., to physicians. Here, the data may be reported to the physicians without assigning the data to any particular wearer of the wearable product 100. In some embodiments, particularly where such local storage of medical data of an individual violates applicable laws (e.g., HIPAA), the health manager 288 may be omitted and the fluid analysis results may instead be stored securely and remotely (e.g., on the cloud, discussed further below).

FIG. 4 shows an example record 300A of the user stored in the cloud 292. The record 300A may contain a plurality of fields 302. For example, in an embodiment, the record 300A may include a field 304 for the name of the user, the fluid analysis results 308 compiled by the health screener 210, the date and time 310 at which the analysis occurred, any alert 318 generated by the alert generator 224, any recommendation 320 generated by the recommendation generator 218, etc. The user (or a person acting on the user's behalf) may provide at least some of this information when he downloads and installs the corresponding mobile application 284 onto the monitor 150 (e.g., the user may provide his name 304 (John in this example) upon installation of the mobile application 284). Some fields in the user record 300A (e.g., the health screener results 308) may be generated once the fluid analysis is complete. When the user record 300A is completed, it may be securely stored in the cloud 292.

The FIG. 4 record 300A shows, for example, that a user named John voided his urine on Nov. 1, 2016 at 2:00 pm. The record 300A also indicates that the user's health screener results 308 indicate high sugar levels, and that an alert 318 and a recommendation 320 about same was conveyed to the user 270.

In some embodiments, in generating an alert 318 and/or a recommendation 320, the alert generator 224 and the recommendation generator 218 of the investigative computer 200 may respectively take into account the user's historical records 300A-300N. For example, the alert generator 224 may not generate an alert 318 even where the urinalysis of the user 270 indicates that the user 270 has diabetic indications, where the user records further indicate that the user 270 has recently been alerted about same a plurality of times. In some embodiments, the alerts 318 communicated to the mobile device 150 may include "read-receipt" functionality so that the software 208 can check whether the alerts 318 are timely viewed by the user 270 (or authorized third party). If the alerts are not timely reviewed, the alert generator 224 may resend same and may cause the mobile device to ring (and/or vibrate). The artisan will appreciate that the communications (e.g., alerts 318, recommendations 320, etc., may be communicated from the investigative computer 200 to the monitor 150 in any suitable manner (e.g., over Bluetooth, via text, over e-mail, over voicemail, direct voice response, alarm annunciators, TCP/IP, UDP, etc.).

Moving on, the analysis portal 118 may be incorporated into a number of different wearable products 100. The exemplary wearable products 100 discussed below are meant to provide a better understanding of the invention, but the invention is not limited to these embodiments.

Figure 5:
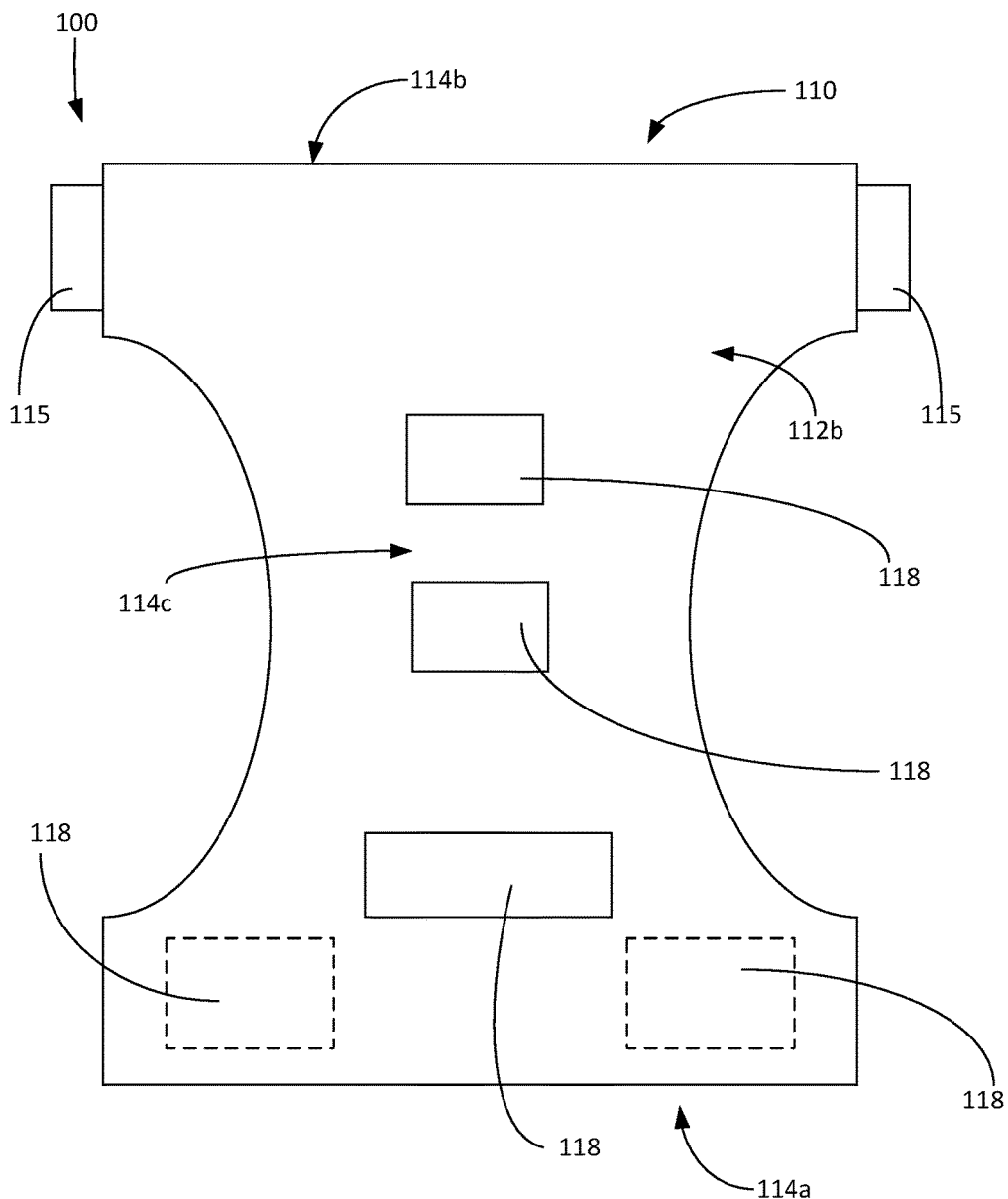
FIG. 5 illustrates an example of a wearable product as a diaper incorporating the analysis portal of FIG. 1.
Figure 6:
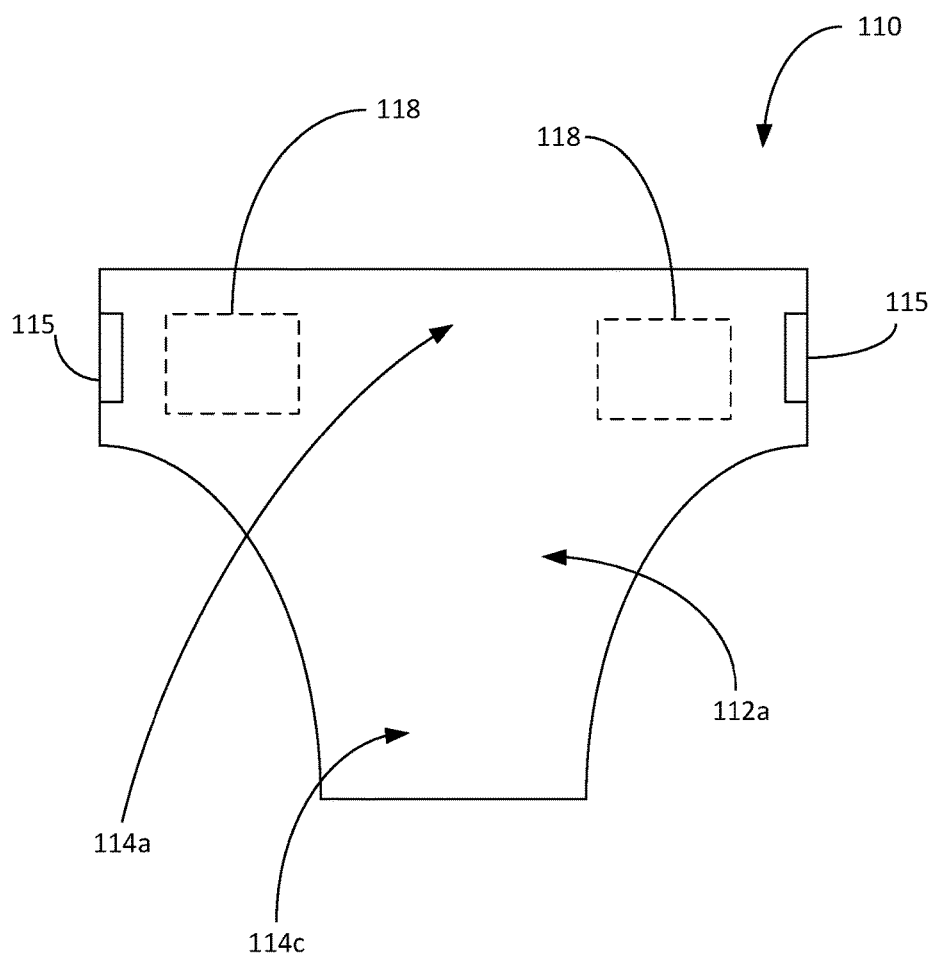
FIG. 6 shows a front view of the diaper of FIG. 5.
Figure 7:
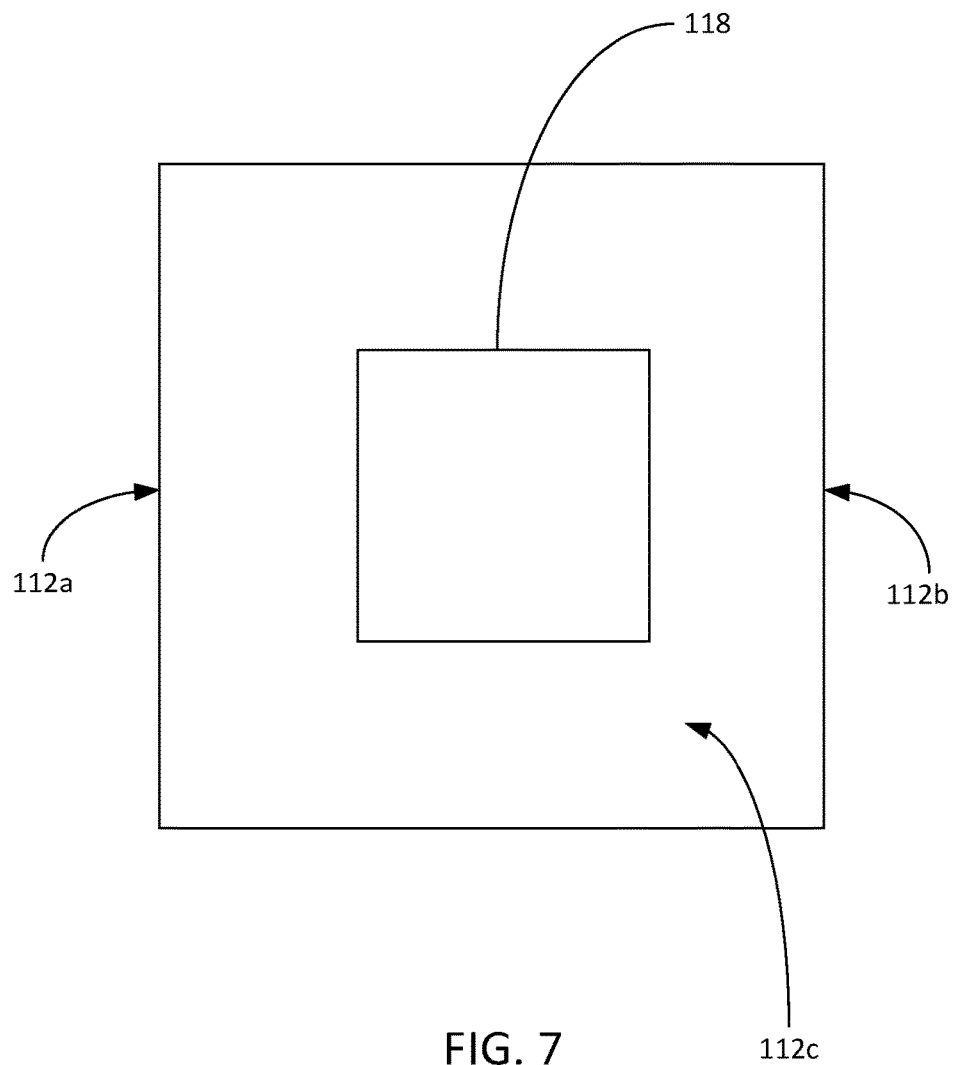
FIG. 7 shows a cross-sectional view of the diaper of FIG. 5.

In one embodiment, shown in FIGS. 5-7, the analysis portal 118 is incorporated into a diaper 110. The diaper 110 has an outside surface 112a and a skin contact surface 112b having at least one absorbent layer 112c disposed between the outside surface 112a and the skin contact surface 112b. The diaper 110 has a front end 114a and a rear end 114b with a central area 114c located between the front end 114a and the rear end 114b.

The diaper 110 is configured to fit securely to a wearer so that bodily excretions and other fluids are contained within the diaper 110. To this end, various contours and fastening mechanisms, whether now known or later developed, may be used. Tabs 115 are illustrated, and may have, for example, hook and loop fasteners or adhesive.

The sensors 120 in the analysis portal 118 may be contact or non-contact sensors 120 as known by those skilled in the art. In embodiments where the sensors 120 are contact sensors, the analysis portal 118, which may be manufactured to have a small surface area (e.g., less than 0.5 cm×0.5 cm) may simply be placed between the user and the wearable product 100, in this case the diaper 110. It may, however, be preferable for the sensors 120 to be non-contact sensors 120. The diaper 110 may have a pocket located in the central area 114c. The pocket may be formed between the at least one absorbent layer 112c and the skin contact surface 112b, for example. The analysis portal 118, equipped with one or more sensors 120, may be disposed in the pocket for receiving and analyzing the wearer's urine, as described herein. Alternately, especially where the analysis portal 118 is designed for single-use applications, the diaper 110 may be manufactured with the analysis portal 118 disposed within the absorbent layer 112c. Absorbent layers may also contain embedded sensing and communication integrated circuitry (e.g. sensory input Radio Frequency Identification (RFID) devices, near-field communication devices with analog-to-digital conversion, microcontrollers, analog and optical systems on-chip, etc.).

As noted above, it is desirable to maintain the cleanliness of the analysis portal 118 to the extent possible in order to ensure that the results are as accurate as possible. In embodiments where the analysis portal 118 is reusable, once the diaper 110 is soiled, using sanitary methods well known to those skilled in the art, the analysis portal 118 may be removed from the diaper 110, cleaned, and placed into the pocket of a clean diaper 110. This process may be followed for the life of the analysis portal 118 (or for so long as it is desirable to obtain information from the analysis portal 118).

As noted herein, many types of sensors 120 may be incorporated into the analysis portal 118. For the sake of example only, an analysis portal 118 in a diaper 110 may be equipped with a moisture sensor 120. The moisture sensor 120 may routinely check for moisture, and may activate a response (e.g., an alert) once moisture is detected.

The alert generator 224 via the transmitter 130 may send an alert message to the monitor 150, which may be displayed on the output device 153, that lets the person receiving the alert know that moisture is detected. The recommendation generator 218 may additionally send a recommendation to the monitor 150 to change the diaper 110. In embodiments, the alert generator 224 may be a part of the analysis portal 118, and an alert (e.g., a sound) may be activated directly from the analysis portal 118 without the need for a remote monitor 150.

Further, the diaper 110 may have at least one pressure sensor 120. Similar to the moisture sensor 120, the pressure sensor 120 may communicate with the monitor 150 via transmitter 130 (or with an alert output device forming a part of or a distributed communication with the analysis portal). The pressure sensor 120 may be located in the diaper 110 in an area where the wearer may be likely to apply pressure with the wearer's weight. The transmitter 130 sends an alert from the alert generator 224 to the receiver 152 in the monitor 150 when the pressure sensor 120 detects a predetermined amount of pressure, or a loss of pressure. Where it is desirable for the wearer to remain in a specific location or position, the pressure sensor 120 may be configured to initiate an alert via the alert generator 224 when the pressure sensor 120 detects a loss of pressure. In other embodiments where it is desirable for the wearer to move, the pressure sensors 120 may be configured to initiate an alert when the sensor 120 determines there has not been movement for a predetermined amount of time. Pressure sensors may be implemented utilizing traditional discrete devices as well as strain-gauge monitoring of material displacement within the analysis portal's system components (e.g. utilizing wheatstone bridge techniques).

Upon the receiver 152 receiving an alert, the processor 151 may cause the output device 153 to provide information regarding the pressure alert to the user. In some embodiments, the processor 151 may activate the output device 153 only if multiple alerts are received over a given amount of time. Along with, or instead of, information regarding the alert(s), the output device 153 may provide a recommendation or action based on the alert(s).

For use with adults, the pressure sensor 120 may, for example, aid in the prevention of bedsores (in one place for too long) or falling (unaided movement). For use with a child, a parent may be alerted that the child has been in one position for too long, or that the child has moved from its previous position. By locating the pressure sensor 120 proximate a front end 114a of the diaper 110, the processor may determine if the child remains on his stomach for an extended period of time. As stomach sleeping is associated with an increased risk for Sudden Infant Death Syndrome (SIDS), an appropriate alert through the output device 153 may help reduce the risk for SIDS. Where appropriate, a motion sensor 120 could be used in place of—or in addition to—the pressure sensor 120 to ensure that a wearer is engaging in an appropriate amount of movement. Additional controlled response modes may provide algorithm cyclical stimulus through the output device 153 on a periodic or event driven basis. For example, an infant in distress may be identified by a sensory identification indicating lack of normal breathing rhythm which may result in a cycling controlled motion response, haptic pulsation output stream, or an auditory response to resolve the detected, suspected, or anticipated alert status. The resulting initiation of this cyclical algorithm may progress for an extended period of time and the alert response algorithm may be managed and potentially concluded by the use of a proportional-integral-derivative (PID) loop control or other closed-loop resolution method. The status of the response algorithm may be communicated in real-time or block-status reports as a pre-alarm indicator to remote receiving devices.

The alerts and recommendations, however, may be much more sophisticated. For example, in persons that are diagnosed with Type I diabetes, the software 208, together with a respective sensor 120, health screener 210 (e.g., with the appropriate module 212), and alert generator 224, may detect high blood sugar and determine an insulin dosage which would be appropriate to correct the high blood sugar. An alert may then be initiated which both signals to the parent or other authorized third party that the wearer has high blood sugar and recommends a correction insulin bolus to return the blood sugar to appropriate levels.

While diapers 110 are routinely understood as being worn by persons experiencing incontinence, they are also used by persons in the ordinary course of business, e.g., astronauts during space missions. NASA (and other government or civilian entities) may be able to use diapers 110 imbedded with analysis portals 118 in order to monitor the health of the astronauts during space missions, and especially while astronauts conduct space walks. The biological information that may be gathered may be extremely useful in planning for future space flight, especially to distances beyond Earth's orbit and extended-length space missions.

Figure 8:
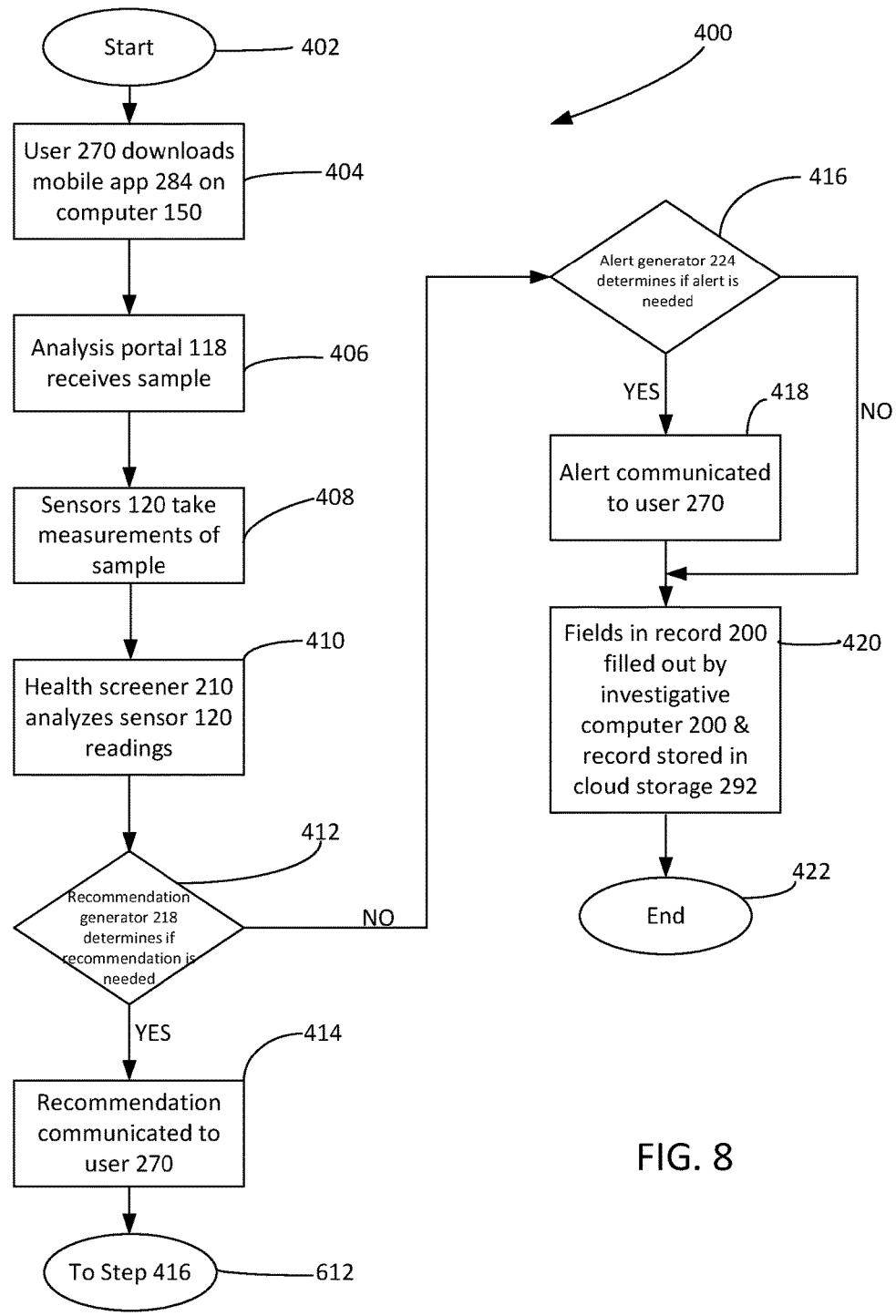
FIG. 8 illustrates an exemplary method of using the diaper with an analysis portal.

FIG. 8 shows an example method 200 of using the diaper according to an embodiment. The method 400 may begin at step 402. At step 404, the user 270 may download and install on his mobile computer 150 the mobile application 284. In so doing, the user 270 may provide and/or the application 284 may otherwise ascertain certain identifying information, such as the name 304 of the user 270, a biometric sample 316 against which subsequent biometric samples provided by the user 270 are to be compared, etc. The artisan will understand that the user 270 may download and install the mobile application 284 on his mobile computer 150 prior to the device 118 being placed in service.

At step 406, the user 270 may void his urine on the analysis portal 118. At step 408, and as discussed above, the sensors 120 may take various measurements associated with the urine (e.g., sensor 120 may determine the sugar content of the urine, sensor 120 may determine the temperature of the urine, etc.). At step 410, the health screener 210 of the investigative computer software 208 may analyze these readings from the sensors 120 to determine various characteristics 423 of the urine of the user (e.g., the sugars module 212F may evaluate the readings from the sugar sensor 120F to determine whether the fluid urine contains normal or abnormal sugar levels, etc.).

At step 412, the recommendation generator 218 may determine whether the analysis indicates that a recommendation (e.g., recommendation 320, see FIG. 7) is to be generated for the user 270. If so, at step 414, the recommendation generator 218 may communicate the recommendation 320 to the user 270. For example, the recommendation generator 218 may transmit the recommendation 320 to the monitor 150. In embodiments, and as discussed above, when determining whether to generate a recommendation, the recommendation generator 218 may take into account the historical records of the user 270 stored on the cloud 292. If the recommendation generator 218 determines that no recommendation is to be generated, the method 400 may move from step 412 directly to step 416.

At step 416, the alert generator 224 may determine whether results of the urinalysis are cause for alarm such that an alert notification (e.g., alert notification 318, see FIG. 7) needs to be communicated to the user 270. If so, at step 418, the alert generator 224 may communicate an alert to the user 270. As discussed immediately above for the recommendation 320, the alert 318, if generated, may be communicated to the user 270 via his monitor 150. In embodiments, when determining whether to generate an alert, the alert generator 224 may take into account the historical records of the user 270 stored on the cloud 292, or user preferred alerts (e.g., if the diaper is wet, the user (e.g., parent) may want to simply know that). If the alert generator 224 determines that no alert is to be generated, the method 400 may move from step 416 directly to step 420.

At step 420, the fields (e.g., the fields 302 in the user record 300A) may be filled out by the investigative computer 200, and the user record 300A may be securely stored on the cloud storage 292. The user record 300A stored on the cloud 292 may be encrypted, password-protected, and/or otherwise secured such that it is only accessible to authorized personnel and computing devices. In embodiments, the user record 300A, or portions thereof, may also be transmitted to the mobile computing device 150. The method 400 may then end at step 422.

In some embodiments, the user 270 may be charged a fee to download and use the mobile application 284 to interact with the analysis portal 118.

The analysis portal 118 and the other components may be powered by standard AC power (e.g., 110V), by batteries, and/or other means (e.g., capacitive, inductive, optical, thermal, vibrational, electromagnetic, radio-frequency, etc.).

In some embodiments, more than one analysis portal 118 may be associated with a wearable product 100. For example, one analysis portal 118 may be situated at a first position as shown in FIGS. 5-6, and one or more analysis portal(s) 118 may be situated at a second position. In the example of a diaper 110, an analysis portal 118 configured to take and examine fluid samples may be located in an area that is desirable for such fluid intake. An analysis portal 118 configured to recognize movement or pressure changes may be located in another desirable area.

Figure 9:
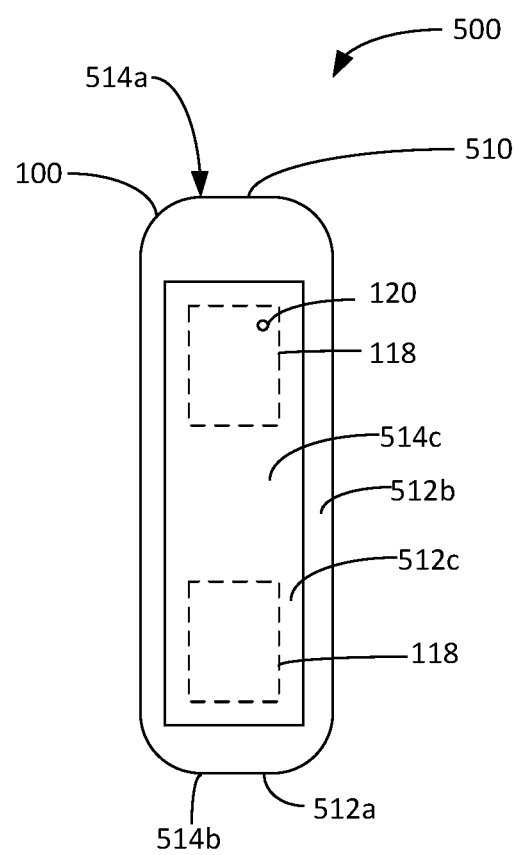
FIG. 9 illustrates another example of a wearable product as a bandage incorporating the analysis portal of FIG. 1.
Figure 10:
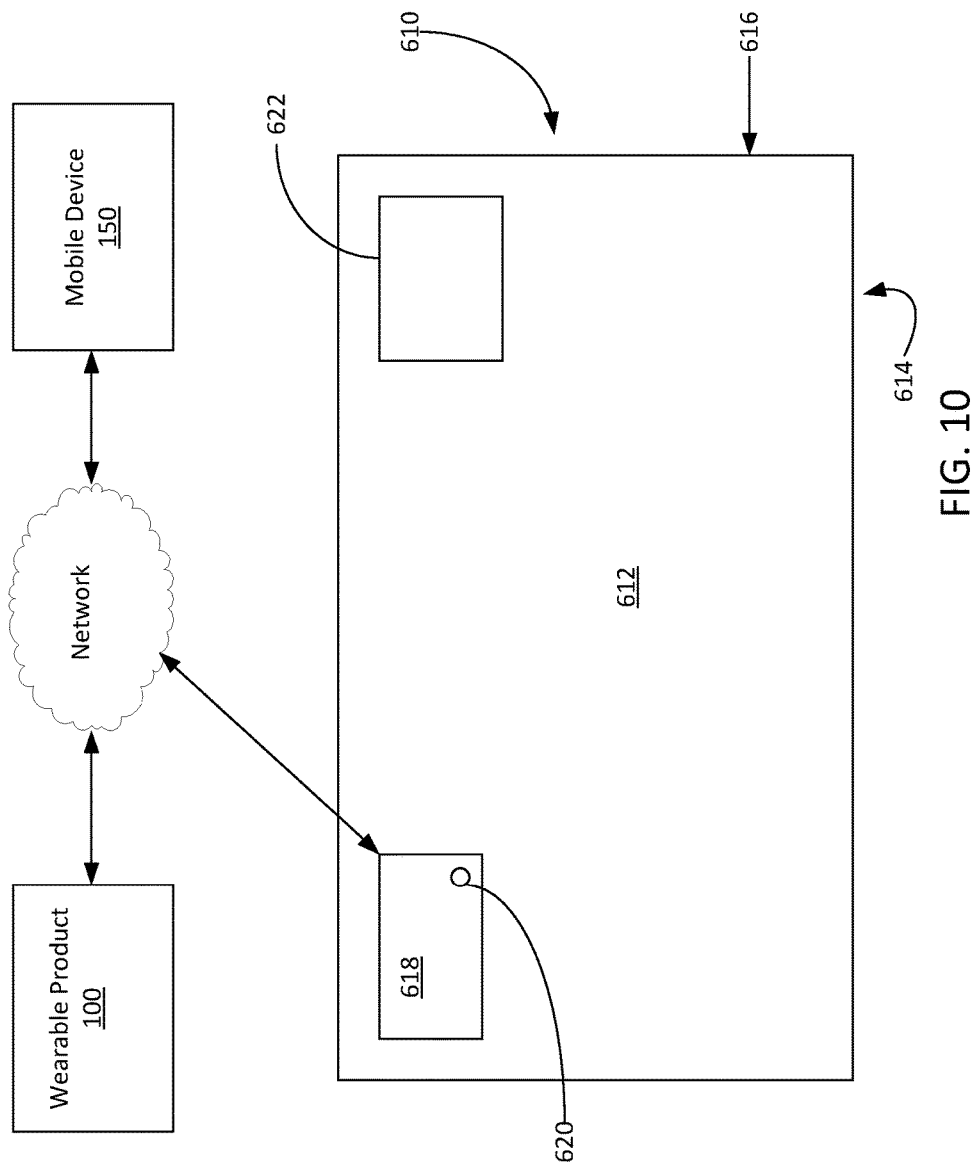
FIG. 10 illustrates a pad according to still another embodiment of the invention.

In another embodiment 500, illustrated in FIGS. 9-10, the wearable product 100 is a bandage 510. The embodiment 500 is substantially similar to the embodiment 100, except as specifically noted or shown, or as would be inherent. Further, those skilled in the art will appreciate that the embodiment 100 (and thus the embodiment 500) may be modified in various ways, such as through incorporating all or part of any of the various described embodiments, for example. For uniformity and brevity, reference numbers between 500 and 599 may be used to indicate parts corresponding to those discussed above numbered between 100 and 199, though with any noted or shown deviations.

Embodiment 500 includes a bandage 510 and a monitor 450. The bandage 410 has an outside surface 512a and a skin contact surface 512b. The bandage 510 may further have at least one absorbent layer 512c disposed between the outside surface 512a and the skin contact surface 512b. The bandage 510 has a first end 514a and a second end 514b having a central area 514c located between the first end 514a and the second end 514b.

An analysis portal 118 may be configured to be disposed in or on the bandage 510, and includes at least one sensor 120, such as a moisture sensor, chemical sensor, pressure sensor, motion sensor, olfactory sensor, biological impulse (e.g, EEG, EKG, localized nerve impulse, etc.) or any other appropriate sensor now known or later developed. In one embodiment, the sensor 120 is a chemical sensor. The chemical sensor operates similar to the sensors 120 described above. The chemical sensor 120 may be placed on the skin contact surface 512b, or it may be inserted between the skin contact surface 512b and the outside surface 512a. Another example embodiment may include both the chemical sensor 120 and a moisture sensor 120.

The chemical sensor 120 may be configured to detect at least one chemical that is associated with an infection from a wound. Those skilled in the art will appreciate that one sensor 120 capable of detecting multiple chemicals may be used, or multiple chemical sensors 120 that detect at least one chemical may be used. The chemical sensor 120 is placed in the bandage proximate the wound so that chemicals from the wound may be detected.

As discussed with other sensors 120, the chemical sensor may routinely check for chemicals, or may activate once a chemical has been detected. In one embodiment, the chemical sensor 120 may alert the user of a deviation from a predetermined specified range. When the chemical sensor 120 detects sufficient amounts of a target chemical, the alert generator 224 sends an alert to the user. Alerts may result in a controlled system response that performs a pre-diagnosed or dynamically adaptive treatment regimen (e.g. metered drug dosage, cleansing agent, air "breathing" mode, etc.). Accordingly, the monitor 150 may be included as part of the analysis portal 118. The output device 153 of the monitor 150 may include a bladder for holding one or more drugs or ointments for treating a wound (e.g., iodine, merbromin, neomycin sulfate, etc.) and configured to deliver the drug or ointment to the area of the wound. When the alert is generated by the alert generator 224, the output device 153 may thus be activated, and the correct drug or ointment may be delivered from the bladder to the area near the wound for treatment. The user may therefore not be required to remove the bandage in order to receive continuing treatment for a wound.

It shall be understood that "bandage" includes dressings such as Band-Aids, gauze, wraps, etc. for protecting wounds, and further includes orthopedic casts, splints, and other types of mechanisms used for protecting and aiding in the healing process.

The wearable products, including but not limited to the diaper and the bandage discussed above, may act as a single product, or may be incorporated into a broader system 500. As described herein, in one embodiment, the sensors 120 in the wearable product 100 may be in communication (e.g., wireless communication) with a pad 610, which may be configured to interact with the wearable product 100 in various ways. In other embodiments, the pad 610 may act as a stand-alone device.

In one embodiment, the pad 610 includes a contact surface 612 and a bottom surface 614 defining an interior area 616. An electrical panel (e.g., a printed circuit board) 618, including but not limited to sensors 620, speakers, and/or vibrating motors may be housed in the interior area 616 and are operational to allow the pad 610 to selectively provide vibrations to a user. The sensors 620 may include proximity sensors, pressure sensors, and/or any other type of sensors discussed herein or that are now or later known to those of skill in the art. The electronics 618 may be powered using any known source, including electrical energy via a wired connection to an outlet or from one or more batteries, etc. Functions of the pad 610 may be further illustrated by means of the several non-limiting examples set forth below.

In one embodiment, the pad 610 may include pressure sensors 620 and/or proximity sensors 620, among others, for monitoring the location and/or movement of a wearer. This may be particularly useful in hospitals where it is sometimes desirable to prevent sudden, or independent, movement of a patient. The pad 610 may be placed, for example, on a surface upon which the wearer may lay. Electronics 618 (e.g., sensors 620 such as pressure sensors, proximity sensors, etc., and corresponding components to make the sensors functional known by those of skill in the art) in the pad 610 may allow the pad 610 to recognize when a wearer is at or near the pad 610. The sensors 620 in the pad 610 may be configured to send a signal, or cause a signal to be sent, if the sensors 620 detect that the wearer has moved a particular threshold distance away from the pad 610 (e.g., 6 inches, 1 foot, etc.) or no longer detect a requisite amount of indicating that the wearer has moved.

In some embodiments, the pad 610 may be further configured to vibrate (e.g. via the vibrating motor(s), electromagnetic or piezo-element annunciators, polymer haptic transducers, etc.). The vibrating motor 622 may have multiple modes to increase and decrease the intensity of the vibrations. The vibrations in the pad 610 may be soothing, and as described below, the vibrations may further provide additional health benefits, especially in adults. As mentioned above, the pad 610 may be operable by itself, or it may be configured (e.g., via the electronics 618) to communicate with a wearable product 100. In embodiments where the pad 610 is configured for operation apart from the wearable product 100, the motor 622 may be activated with a switch, which may be physically located on the pad 610 itself, or may be controlled through a mobile device 650 (substantially similar to mobile device 150). In embodiments where the pad 610 is configured for communication with a wearable product 100, the pad 610 may receive information or alerts from the wearable product 100, causing the pad 610 to vibrate. For example, the pad 610, via electronics known to those in the art, may be programmed to receive alerts from pressure sensors 120 in the wearable device 100. When the pad 610 receives an alert from the pressure sensor that the wearer has not moved in a certain predetermined period of time, the vibrating motor 622 may be actuated to provide stimulation to the wearer.

In another embodiment, the pad 610 may be configured to interact with the bandage 510 to provide vibration therapy to a person with broken bones or other ailments. Vibration therapy is known to prevent bone loss by transmitting vibrations directly through the body. It is believed that by sending vibrations through the body, it is possible to, among other things, increase bone density, increase muscle mass, improve circulation, reduce joint pain, reduce back pain, alleviate stress, and boost metabolism. The effectiveness of the treatment may be dependent on the intensity of the vibrations, and the direction in which the vibrations occur. Vibrations may occur in the vertical (z) direction, the lateral (y) direction, and/or in the longitudinal (x) direction, and may range in intensity from barely able to be perceived (e.g., micro-vibrations) to high intensity. The vibration therapy may be localized to a specific area, or may be whole-body focused.

In embodiments, sensors 620 in the pad 610 (e.g., proximity sensors, pressure sensors, etc.) may communicate with sensors 120 in the bandage 510 to provide vibration therapy. Such vibration therapy, as noted above, may aid in the body's ability to produce osteoblasts, which in turn produce bones. By sending vibrations to a localized area on the body in need of bone regrowth, such as when a broken bone is in a cast, the healing process may be expedited, and the ultimate end result may be improved.

The pad 610 may be strategically located such that vibrations are provided at times when it is convenient for the person to receive the vibrations. For example, the pad 610 may be placed on the bed in the general area of the bandage 510 (e.g., near the head of the bed for extremities on an upper portion of the body such as collar bones, arms, etc., or near the foot of the bed for extremities on a lower portion of the body such as knees, ankles, etc.). It shall be understood that the pad 610 may be transportable.

As briefly noted above, and is understood by those of skill in the art, the pad 610 may be further equipped with a processor, memory, storage, programming, and a networking device (part of the electronics 618). The programming may be customized such that the vibrations may be turned on or off at various intervals. For example, the motor 622 may be equipped with a timer which may be set for a particular interval (e.g., 30 minutes, 1 hour, 2 hours, etc.). Additionally, or alternately, the programming may cause the vibrations to pulse, allowing the user to receive vibrations of varying intensity. The programming may be controlled remotely through a smart phone or other corresponding device.

In still another embodiment, the pad 610 may stand alone as a singular device. Studies have shown that benefits of vibrations, such as the vibrations described above, may be useful for treating ailments such as erectile dysfunction (ED). Medications used to treat such ailments may have undesirable and often alarming side effects. To date, studies have shown that low-intensity extracorporeal shockwave treatment (LI-ESWT) may be used to improve cavernosal arterial flow, which would in turn improve erectile function. The goal is to increase blood flow generally, as it is known that decreased myocardial blood flow has an effect on a male's ability to achieve and/or keep an erection. Treatments of ED using LI-ESWT have previously been focused directly on the target tissue. For example, Gruenwald et al. (Shockwave Treatment of Erectile Dysfunction, Ther. Adv. Urol., 2013 April; 5(2):95-99), studied 20 men, and provided a treatment protocol that consisted of applying 300 SWs (0.09 mJ/mm$^2$) to each of five different sites: three along the penile shaft, and two at the crural level. The men underwent two treatment sessions per week for 3 weeks, had a three-week break, and then returned for a second 3-week treatment period. Such a treatment protocol is clearly onerous for the person receiving treatment. Other devices have been approved by the FDA that likewise require direct nerve stimulation to dorsal and ventral surfaces of the penis. Yet again, these devices are burdensome, both physically and mentally.

It would be desirable to provide the proven beneficial LI-ESWT without requiring the person to see a clinician for multiple treatments, or to have to use a difficult device. The pad 610, may be used to provide such treatment. The pad 610, as described above, may provide vibration therapy to a user by vibrating when the user is in contact with the pad. Here, the pad 610 may be placed on a sleeping surface, for example, between the mattress and the user, to provide vibrations while sleeping. Because the vibrations are not specifically directed to any one area of tissue, the person may experience overall increased blood flow, which may directly affect the individual's ability to achieve and/or maintain an erection. The pad 610 may be placed at a location on the mattress that allows the vibrations to be more closely concentrated in the central part of the body. Due to the pad 610 being in a location that is easily accessible, the treatment may be provided at any time, without requiring the individual to see a clinician or use a specialized tool.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. It will be understood that certain features and subcombinations are of utility and may be employed without reference to other features and subcombinations and are contemplated within the scope of the claims. A skilled artisan may develop alternative means of implementing the aforementioned improvements without departing from the scope of the present invention. Not all steps listed in the various figures need be carried out in the specific order described.

The invention claimed is:

1. A system for monitoring at least one characteristic of a biological material of an individual, comprising:
    a wearable product, the wearable product comprising an outer surface and a skin contact surface; and
    an analysis portal disposed between the outer surface and the skin contact surface, the analysis portal comprising a sensing portion and an investigation portion, the sensing portion including at least one sensor and at least one channel for temporarily retaining the biological material, and the investigation portion comprising a computing device having a health screener;
    wherein:
        the sensing portion of the analysis portal comes into contact with the biological material of the individual;
        the health screener determines at least one characteristic of the biological material;
        the computing device is communicatively coupled to the at least one sensors; and
        the analysis portal further comprises a dispensing unit, the dispensing unit comprising a bladder for holding a medicament, wherein the dispensing unit is configured to release a predetermined amount of medicament based on an evaluation of the at least one characteristic of the biological material.

2. The system of claim 1, wherein the wearable product is a diaper.

3. The system of claim 1, wherein the wearable product is a bandage.

4. The system of claim 1, wherein the sensor is selected from the group consisting of: a moisture sensor, a chemical sensor, a pressure sensor, a motion sensor, and an olfactory sensor.

5. The system of claim 1, further comprising a display.

6. The system of claim 5, wherein the display is remote from the wearable product, and wherein the computing device is configured to wirelessly communicate with the display.

7. The system of claim 6, wherein the display is a mobile device.

8. The system of claim 7, wherein the computing device further includes an alert generator, the alert generator communicates an alert to the individual via the mobile device based on the evaluation of the at least one characteristic.

9. The system of claim 1, wherein the computing device further includes an alert generator, the alert generator communicates an alert to the individual based on the evaluation of the at least one characteristic of the biological material.

10. The system of claim 9, wherein the alert is an auditory alert.

11. The system of claim 9, wherein the alert generator further communicates an alert to a third party.

12. The system of claim 11, wherein the alert transmitted to the third party comprises a recommendation for taking action.

13. The system of claim 1, wherein the sensor is a bacteria sensor.

14. The system of claim 13, wherein the medicament is an anti-bacterial ointment.

15. The system of claim 1, further comprising a pad, comprising a vibrating motor, wherein the vibrating motor is selectively activated to provide vibrations to the individual.

16. The system of claim 15, wherein the pad further comprises at least one of a pressure sensor and a proximity sensor.

17. The system of claim 16, wherein the sensor activates the vibrating motor upon reaching a predetermined threshold.

18. The system of claim 1, wherein the analysis portal is configured for disposable use.

19. The system of claim 1, wherein the analysis portal is configured for multiple uses.

20. The system of claim 1, wherein the dispensing unit further comprises a container for holding a cleansing agent, and wherein the container dispenses the cleansing agent to the sensing portion of the analysis portal.

* * * * *